(12) United States Patent
Odinak et al.

(10) Patent No.: US 7,512,247 B1
(45) Date of Patent: Mar. 31, 2009

(54) WEARABLE WIRELESS EAR PLUG FOR PROVIDING A DOWNLOADABLE PROGRAMMABLE PERSONAL ALARM AND METHOD OF CONSTRUCTION

(76) Inventors: Gilad Odinak, 268 W. Lake Sammamish Pkwy. NE., Bellevue, WA (US) 98008;
Elior Odinak, 268 W. Lake Sammamish Pkwy. NE., Bellevue, WA (US) 98008

( * ) Notice: Subject to any disclaimer, the term of this patent is extended or adjusted under 35 U.S.C. 154(b) by 191 days.

(21) Appl. No.: 11/453,362

(22) Filed: Jun. 14, 2006

Related U.S. Application Data

(63) Continuation-in-part of application No. 10/676,300, filed on Sep. 30, 2003, now abandoned.

(60) Provisional application No. 60/415,708, filed on Oct. 2, 2002.

(51) Int. Cl.
*H04R 25/00* (2006.01)
(52) U.S. Cl. ...................... 381/312; 381/315
(58) Field of Classification Search ................. 381/315, 381/312
See application file for complete search history.

(56) References Cited

U.S. PATENT DOCUMENTS

| | | | |
|---|---|---|---|
| 4,533,986 A * | 8/1985 | Jones | 363/17 |
| 5,253,300 A | 10/1993 | Knapp | |
| 5,566,226 A * | 10/1996 | Mizoguchi et al. | 455/558 |
| 6,067,006 A | 5/2000 | O'Brien | |
| 6,253,871 B1 | 7/2001 | Aceti | |
| 6,819,256 B2 * | 11/2004 | Hampton | 340/691.6 |
| 6,879,695 B2 * | 4/2005 | Maltan et al. | 381/315 |
| 6,906,983 B2 | 6/2005 | Williams et al. | |
| 2004/0063456 A1 * | 4/2004 | Griffin et al. | 455/550.1 |

OTHER PUBLICATIONS

Atmel, 8-bit AVR Microcontroller with 1K Byte Flash ATtiny11 ATtiny 12 pp. 1-8, 46-56 (2003).*

* cited by examiner

*Primary Examiner*—Walter F Briney, III
(74) *Attorney, Agent, or Firm*—Patrick J.S. Inouye; Krista A. Wittman

(57) ABSTRACT

A wearable wireless ear plug for providing a downloadable programmable personal alarm and method of construction are described. An alarm circuit is integrated with a self-contained power source. A randomly accessible memory is included to provide general purpose storage. A leadless interface is provided to externally receive a user-settable time interval and a programmable alarm tone, which are both stored into the memory. A clock circuit activates and times the user-settable time interval. A wireless interface receives a radio frequency alarm signal. An alarm circuit retrieves from the memory and generates the alarm tone through an in-ear speaker, which is triggered by either the clock circuit or the wireless interface respectively upon an expiry of the user-settable time interval and receipt of an alarm signal. The alarm circuit is housed in an ear plug shaped to house the in-ear speaker within an ear canal and to enclose the alarm circuit.

21 Claims, 5 Drawing Sheets

10

15

WEARABLE WIRELESS EAR PLUG FOR PROVIDING A DOWNLOADABLE PROGRAMMABLE PERSONAL ALARM AND METHOD OF CONSTRUCTION

CROSS-REFERENCE TO RELATED APPLICATION

This patent application is a continuation-in-part of U.S. patent application Ser. No. 10/676,300, filed on Sep. 30, 2003, abandoned, which claims priority under 35 USC § 119(e) to U.S. provisional patent application Ser. No. 60/415,708, filed Oct. 2, 2002, the priority filing dates of which are claimed and the disclosures of which are incorporated by reference.

FIELD OF THE INVENTION

The present invention relates in general to electronic ear plugs and, in particular, to a wearable wireless ear plug for providing a downloadable programmable personal alarm and method of construction.

BACKGROUND OF THE INVENTION

Ear plugs are soft plugs that are inserted into the outer ear canal to block ambient sound and environmental noise. Ear plugs are available in various sizes and shapes. Rounded ear plugs fit directly into the outer ear canal and are less prone to falling out of the ear due to movement. Conformable ear plugs generally fit into the cavum conchae of the outer ear to provide a less intrusive form of hearing protection. However, conformable ear plugs are also more apt to fall out if not well-fitted to a particular user's outer ear contours.

Ear plugs are frequently used by people who must sleep in a noisy environment. For example, ear plugs are often used by airplane and train passengers traveling on long trips, sometimes overnight, and who want to sleep to either pass the time or due to an upcoming busy schedule at their destination. Ear plugs are also used by people whose sleep is disturbed each night by ambient noise or a snoring spouse. Ear plugs are also useful to assist concentration of people working in a noisy environment.

The noise reduction or cancellation provided by ear plugs blocks ambient sounds non-discriminately, which can sometimes have unintended side affects. For instance, people who wear ear plugs while sleeping often need to wake up at a certain time and would prefer to use an alarm clock to wake on time. However, the ear plugs can block an alarm clock sound, thereby rendering alarm clock usage meaningless. Furthermore, ear plugs can block emergency or warning signals, such as generated by a fire or burglar alarm, and potentially imperil the wearer.

Overriding ear plugs by simply using a louder signal offers an incomplete solution. For example, an alarm clock with an alarm loud enough to penetrate through the ear plugs is not always practical. On an airplane or train, an extra-loud alarm clock could disturb other passengers, while at home, an extra-loud alarm clock could unnecessarily wake up the user's spouse. Similarly, placing an alarm clock close to a user's ear can be inconvenient, as the user could move away from the alarm clock while sleeping, or impractical, such as on an airplane where physically attaching an alarm clock to a seat could be prohibited.

In the prior art, a personal audible alarm is described in U.S. Pat. No. 6,067,006 to O'Brien, issued May 23, 2000, the disclosure of which is incorporated by reference. An audible alarm is placed in an ear plug or hearing protection device. An audio output is located on a side of the earplug open to or exposed to the user's ear canal. The ear plug includes a battery, clock display, time set switch, alarm set switch, hour set switch, and minute set switch for indicating time of day and alarm time. However, the O'Brien device lacks provisions for external battery recharging and alarm programming and cannot receive downloadable audible alarm tones.

Accordingly, there is a need for an approach to embedding a programmable alarm feature directly into an ear plug.

There is a further need for an approach to providing a programmable alarm feature that can receive and generate an alarm signal independently of ear plug noise reduction or cancellation.

SUMMARY OF THE INVENTION

A wearable wireless ear plug for providing a downloadable programmable personal alarm and method of construction is described. The electronic ear plugs can be used singly or in pairs. Operationally, to use the electronic ear plugs, a user first places the electronic ear plugs in a carrying case and uses a keypad to program timer values. After setting a wakeup or alert time, the user places electronic ear plugs in one or both ears. The electronic ear plugs sound an alarm at the programmed time. In a further embodiment, the electronic ear plugs also sound an alarm upon receiving a wirelessly transmitted alarm signal through an integrated wireless interface.

An embodiment provides an electronic ear plug for providing a programmable audible alarm. An audible alarm circuit includes an interface and a countdown timer. The interface receives and stores a user-settable time interval and at least one programmable alarm tone from an external source into a memory. The countdown timer commences timing upon activation of the user-settable time interval and generates at least one programmable alarm tone responsive to an expiry of the user-settable time interval. An ear plug is shaped on a distal end to be received by an ear and defines a recess on a proximal end housing the audible alarm circuit.

A further embodiment provides a programmable ear plug providing an audible alarm. A removable ear plug is shaped on a distal end to be received by an ear and integrates an audible alarm circuit on a proximal end. A memory maintains a user-settable time interval and at least one programmable alarm tone, which are received over a programming channel. A countdown timer commences timing upon activation of the user-settable time interval and generates the at least one programmable alarm tone responsive to an expiry of the user-settable time interval. A power supply provides power to the memory and the countdown timer and includes a rechargeable power cell and a recharging interface. An external programmer is removably interfaced to the removable ear plug via the programming channel and the recharging interface to recharge the rechargeable power cell.

A further embodiment provides a method for providing a programmable audible alarm through an electronic ear plug. An electronic ear plug is situated relative to a programming interface removably disposed on an external programmer. The electronic ear plug includes a removable ear plug shaped on a distal end to be received by an ear and integrates an audible alarm circuit on a proximal end. A user-settable time interval is programmed via the programming interface and at least one programmable alarm tone is specified into a memory maintained in the electronic ear plug. The electronic ear plug is placed in an ear. The audible alarm circuit commences timing upon activation of the user-settable time interval and generates at least one programmable alarm tone responsive to an expiry of the user-settable time interval.

A further embodiment provides a wearable wireless ear plug for providing a downloadable programmable personal alarm and method of construction is described. An alarm circuit is integrated with a self-contained power source. A randomly accessible memory is included to provide general purpose storage. A leadless interface is provided to externally receive a user-settable time interval and a programmable alarm tone, which are both stored into the memory. A clock circuit activates and times the user-settable time interval. A wireless interface receives a radio frequency alarm signal. An alarm circuit retrieves from the memory and generates the programmable alarm tone through an in-ear speaker, which is triggered by one of the clock circuit and the wireless interface respectively upon an expiry of the user-settable time interval and a receipt of an alarm signal. The alarm circuit is housed in an ear plug shaped distally to house the in-ear speaker within an ear canal and shaped proximally to enclose the alarm circuit.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1A:
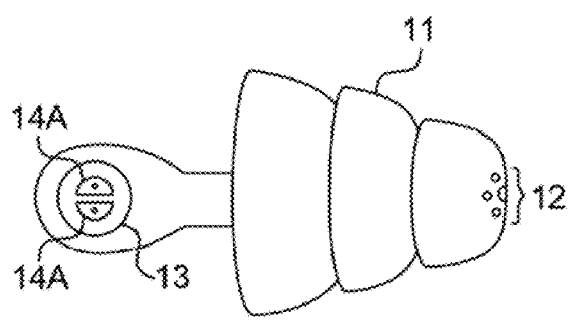
FIGS. 1A-B are plan diagrams respectively showing a front view and a side view of an electronic ear plug for providing a programmable audible alarm, in accordance with the present invention.
Figure 1B:
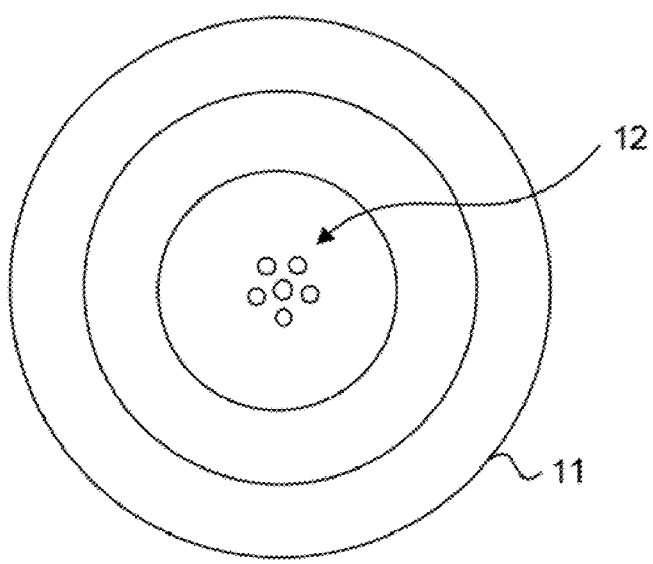

FIGS. 1A-B are plan diagrams respectively showing a front view 10 and a side view 15 of an electronic ear plug 11 for providing a programmable audible alarm, in accordance with the present invention. The electronic ear plug incorporates an electronic countdown timer coupled to a sonic transducer (not shown) that emits audible alarm tones, as further described below with reference to FIG. 4. The electronic ear plug 11 is preferably shaped to fit directly into the ear canal and includes speaker perforations 12 on a distal end facilitating playback of the audible alarm tones. A set of leadless electrical connectors 13, 14A-B on a proximal end facilitate external battery recharging and alarm programming via a carrying case, as further described below with reference to FIGS. 2A-B.

In the described embodiment, the electronic ear plug 11 is soft-coated and shaped to fit directly into the ear canal in the same manner as a conventional ear plug. Alternatively, the electronic ear plug 11 could be shaped to fit conformably into the cavum conchae of the outer ear. The electronic ear plug 11 could be used singly or paired with another electronic ear plug 11. Other shapes and configurations of the electronic ear plug 11 are feasible, as would be recognized by one skilled in the art.

Figure 2A:
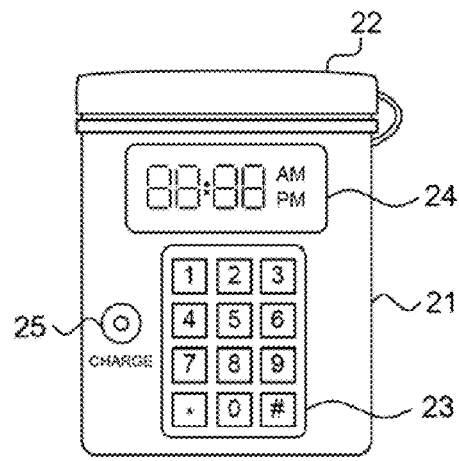
FIGS. 2A-B are plan diagrams respectively showing a side view and a top view of a carrying case for the electronic ear plug of FIGS. 1A-B.
Figure 2B:
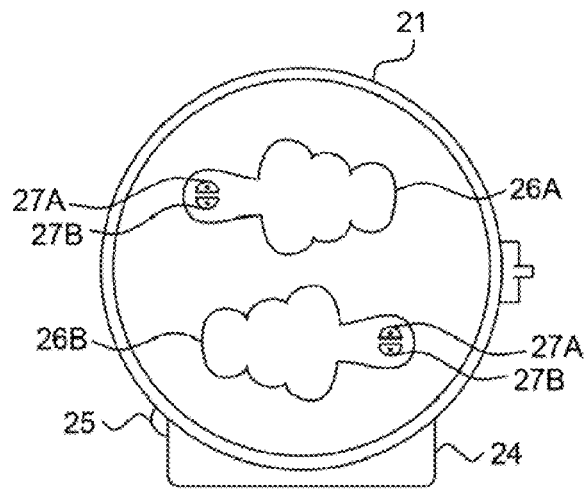

FIGS. 2A-B are plan diagrams respectively showing a side view 20 and a top view 30 of a carrying case 21 for the electronic ear plug 11 of FIGS. 1A-B. The carrying case 21 includes a removable cover 22 that preferably snaps into place. The electronic ear plug 11 can be programmed to playback audible alarm tones, including conventional buzzers, bells voices, music, or other electronically-reproducible sounds. The user enters an alarm time on a keypad 23, which is displayed on a display 24. In the described embodiment, the alarm time is programmed as either an absolute wakeup time, such as 7:30 AM, or as a relative wake up time, for instance, occurring 90 minutes from the present time. Other forms of programming inputs and sources, including interfacing to an external input source, such as a personal computer or cellular telephone, are feasible, as would be recognized by one skilled in the art.

The carrying case 21 also includes a pair of conformal recesses 26A-B for storing each electronic ear plug 11. Each conformal recess 26A-B includes a set of leadless electrical connectors 27A-B that form an electrical connection with the set of connectors 14A-B (shown in FIG. 1A) when each electronic ear plug 11 is placed in the carrying case 21. The electronic connection is used to recharge and program each electronic ear plug 11 through a leadless wired connection. Recharging activity is indicated by a charging light emitting diode (LED) 25 located next to the keypad 23. In a further embodiment, the electronic ear plug 11 is recharged and programmed through inductive coupling, which obviates the need for the leadless electrical connectors 27A-B in the carrying case 21 and the leadless electrical connectors 13, 14A-B on the electronic ear plug 11 itself.

Figure 3:
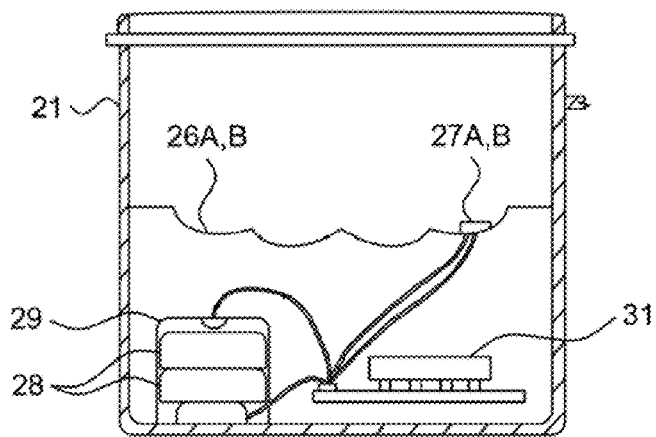
FIG. 3 is a cut-away diagram showing a side cross-sectional view of the carrying case of FIGS. 2A-B.

FIG. 3 is a cut-away diagram showing a side cross-sectional view 35 of the carrying case 21 of FIGS. 2A-B. The carrying case 21 incorporates programming circuitry 31 used to recharge and program each electronic ear plug 11. A set of batteries 28 are received in a battery housing 29 for providing power to the programming circuitry 31. The recharging circuitry includes a step-down converter to provide control over the power source of the alarm circuit and a voltage regulator to generate direct current applied to the power source through the step-down converter. Other forms of recharging circuitry are possible.

Figure 4:
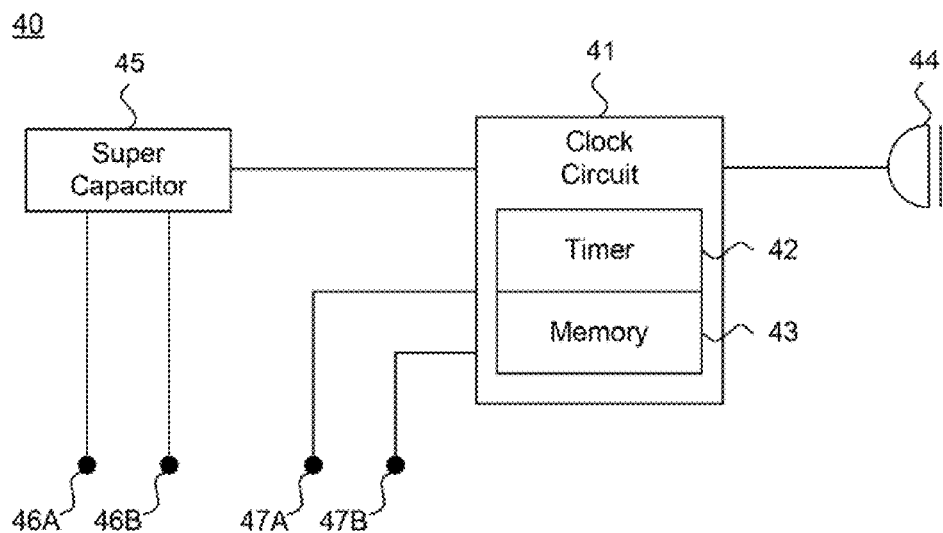
FIG. 4 is a schematic block diagram of the electronic ear plug of FIGS. 1A-B.

FIG. 4 is a schematic block diagram 40 of the electronic ear plug 11 of FIGS. 1A-B. Timer operation is controlled by a clock circuit 41, that includes an internal timer 42 and memory 43 powered by an electrical storage device, such as a super capacitor 45 or rechargeable battery (not shown). The memory 43 stores timer values and the audible alarm tones. The clock circuit 41 is connected to a transducer 44 that generates audible alarm tones. The super capacitor 45 receives a charge from the carrying case 21 (shown in FIGS. 2A-B) via charging connectors 46A-B. The clock circuit 41 receives programming signals from the carrying case 21 via connectors 47A-B. In the described embodiment, the charging connectors 46A-B and the programming connectors 47A-B would be merged into the pair of electrical connectors 14A-B (shown in FIG. 1) to deliver charging and signaling on a single pair of wires, as is known in the art. Finally, the clock circuit 41 can also store audible alarm tones downloaded from the carrying case 21 in the memory 42. Other clock circuit configurations are feasible, as would be recognized by one skilled in the art.

Figure 5:
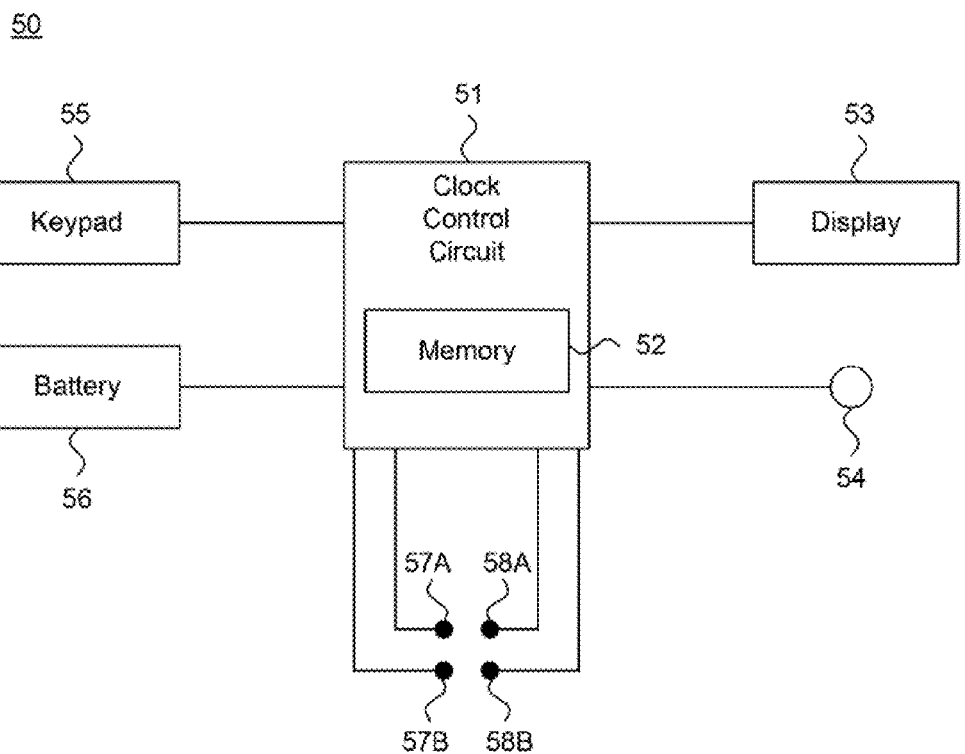
FIG. 5 is a schematic block diagram of the carrying case of FIGS. 2A-B.

FIG. 5 is a schematic block diagram 50 of the carrying case 21 of FIGS. 2A-B. Recharging and programming is controlled by a clock control circuit 51, that includes a memory 52 powered by an electrical storage device, such as a removable battery 56 or external power source (not shown). The memory 52 stores downloadable timer values and audible alarm tones. The clock control circuit 51 receives programming inputs from a user from the keypad 55 and displays specified timer values on the display 53. The clock control circuit 51 also indicates charging activity on the LED 54. The clock control circuit 51 delivers a charge to each electronic ear plug 11 (shown in FIGS. 1A-B) via connectors 57A-B. Finally, the clock control circuit 51 sends programming signals and downloads audible alarm tones stored in the memory 52 via connectors 58A-B. In the described embodiment, the charging connectors 57A-B and the programming connectors 58A-B would be merged into the set of electrical connectors 27A-B (shown in FIG. 2B) to deliver charging and signaling on a single pair of wires, as is known in the art.

The electronic ear plugs 11 can be used singly or in pairs. Operationally, to use the electronic ear plugs 11, a user first places the electronic ear plugs 11 in the carrying case 21 and uses the keypad 23 to program timer values. After setting a wakeup or alert time, the user places the electronic ear plugs 11 in one or both ears. The electronic ear plugs 11 sound an alarm at the programmed time.

Although the described embodiment incorporates a carrying case 21 that also serves as a recharging and programming device, alternative devices and adapters could be used. For example, a mobile telephone adapter could incorporate a telephone keypad display and provide electric power to recharge and program the electronic ear plugs 11. Also, the electronic ear plugs 11 could include built-in programming input control and logic in addition to the carrying case 21. Finally, the carrying case 21 could recharge each electronic ear plug super capacitor 45 using induction or disposable batteries could be employed.

Figure 6:
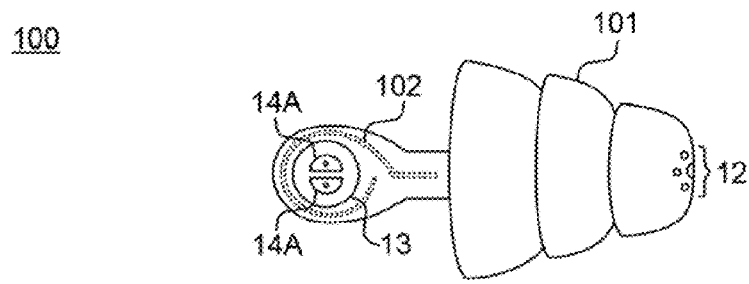
FIG. 6 is a plan diagram showing a front view of a wearable wireless ear plug for providing a downloadable programmable personal alarm, in accordance with a further embodiment.

The self-contained in-ear alarm functionality provided by the electronic ear plug 11 can be supplemented through an integrated wireless interface. FIG. 6 is a plan diagram showing a front view 100 of a wearable wireless ear plug 101 for providing a downloadable programmable personal alarm, in accordance with a further embodiment. The wireless ear plug 101 incorporates both an electronic countdown timer coupled to a sonic transducer (not shown), as further described above with reference to FIG. 4, and a wireless interface (not shown) to receive a radio frequency alarm signal, as further described below with reference to FIG. 9. The wireless ear plug 101 emits audible alarm tones triggered by the clock circuit upon an expiry of a user-settable time interval and by the wireless interface upon the receipt of an alarm signal. The proximal end of the ear plug 101 includes an embedded antenna 102. The radio frequency alarm signal can be a remotely scheduled alarm signal, such as for a wireless alarm clock, or an asynchronous alarm signal. In addition, either the programmed alarm tones previously downloaded into the on-board memory, or a real time alarm tone transmitted as part of the alarm signal could be played through the wireless ear plug 101, and can be either a sound or voice message.

Figure 7:
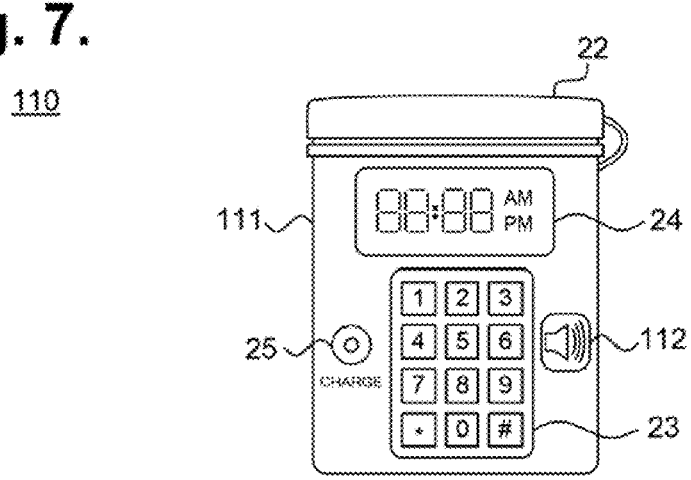
FIGS. 7 and 8 are plan diagrams respectively showing a side view and a top view of a carrying case for the wireless ear plug of FIG. 6.
Figure 8:
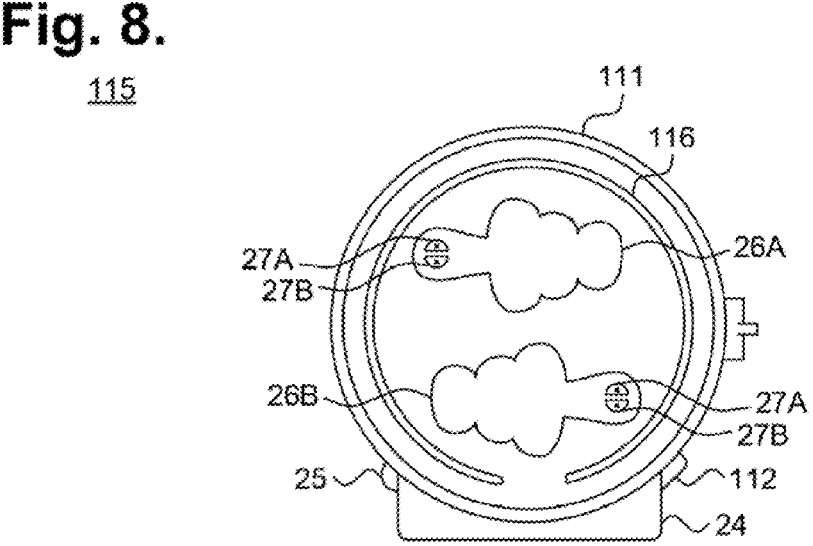

In one embodiment, the radio frequency alarm signal is remotely triggered by a carrying case for storing, recharging, and programming the wireless ear plug 101. FIGS. 7 and 8 are plan diagrams respectively showing a side view 110 and a top view 115 of a carrying case 111 for the wireless ear plug 101 of FIG. 6. An antenna 116 is embedded into the carrying case 111 and is internally connected to a wireless transmitter (not shown). A radio frequency alarm signal is sent from the carrying case 111, either as scheduled per a user-entered alarm time, or manually when a "panic" button 112 located next to the keypad 23 is pressed. In a further embodiment, the alarm signal can be triggered by a third party radio frequency transmitter in response to a person, event, or other stimuli, for instance, a smoke detector alarm or personal page sent by telephone. Other types of alarm signal triggers are possible.

Figure 9:
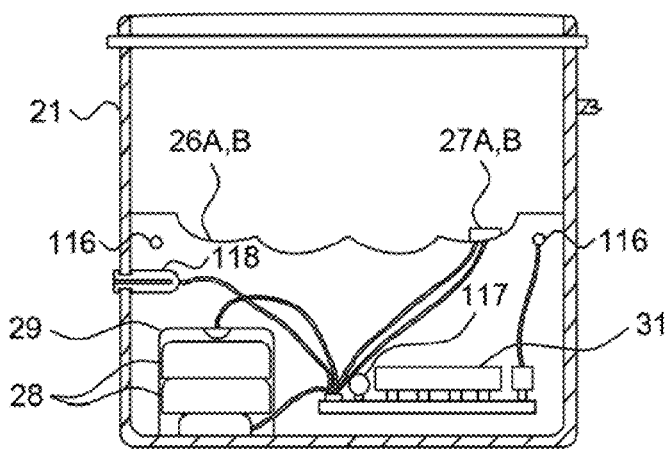
FIG. 9 is a cut-away diagram showing a side cross-sectional view of the carrying case of FIGS. 7 and 8.

Using the carrying case 111 as an alarm signal trigger allows the wireless ear plug 101 to continue to operate wirelessly within an environment that blocks external radio frequency signal receipt, such as within a building or train tunnel. FIG. 9 is a cut-away diagram showing a side cross-sectional view 120 of the carrying case 111 of FIGS. 7 and 8. The programming circuitry 31 includes a wireless transmitter 117 and is connected to the embedded antenna 116 to enable transmission of the radio frequency alarm signal. The wireless transmitter 117 wireless interfaces to the wireless ear plug 101 using short-range radio frequency transmission, such as provided through the Bluetooth wireless and IEEE 802.11-compliant communication protocols. Other communication protocols are possible. The carrying case 111 also includes a connector 118 that enables the wireless transmitter 117 to receive an external trigger over a wired connection that could be interfaced to, for example, a smoke detector or burglar alarm system. Other types of external triggers are possible.

Figure 10:
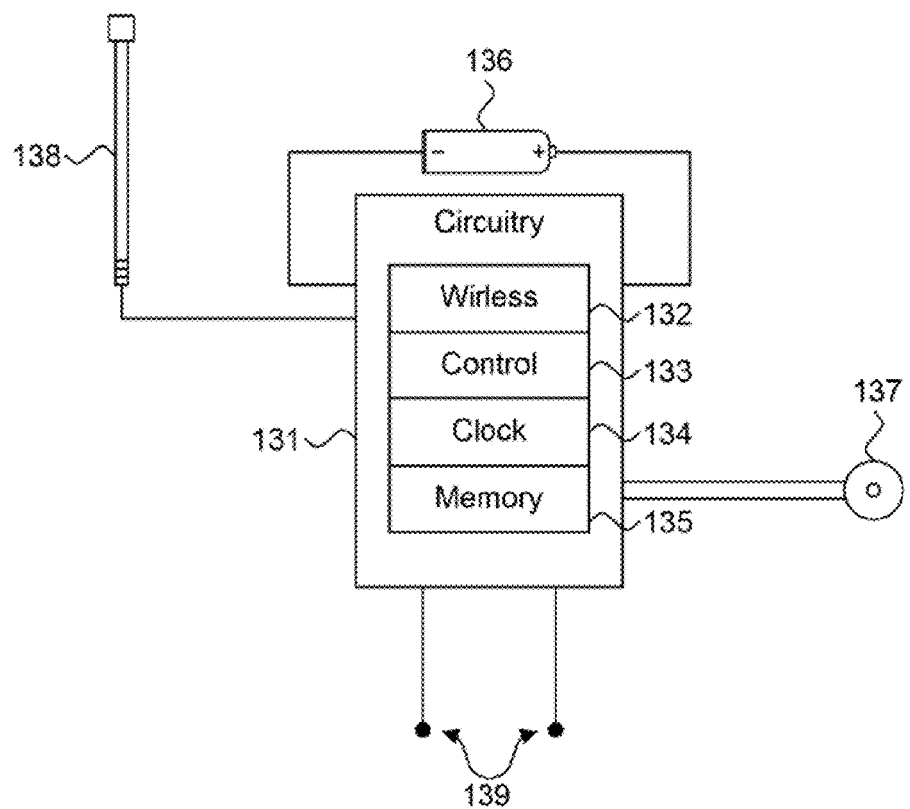
FIG. 10 is a schematic block diagram of the wireless ear plug of FIG. 6.

The wireless interface enables the wireless ear plug 101 to receive and generate an alarm signal independently of ear plug noise reduction or cancellation. FIG. 10 is a schematic block diagram 130 of the wireless ear plug 101 of FIG. 6. The wireless ear plug 101 includes circuitry 132 that implements a wireless interface 132, control 133, clock 134, and memory 135. The circuitry is powered by a portable power source 136, such as a battery or super capacitor, that can be recharged through a leadless interface 139. The wireless interface 132 is connected to an antenna 138, which is embedded into the wireless ear plug 101, and interfaces to radio frequency transmitters using short-range radio frequency transmission, such as provided through the Bluetooth wireless and IEEE 802.11-compliant communication protocols. In a further embodiment, the wireless interface 132 interfaces to radio frequency transmitters using long-range radio frequency transmission, such as frequency modulation, either in addition to or in lieu of short-range radio frequency transmission. Other communication protocols are possible.

The remaining circuitry supports basic alarm signal processing. The control circuitry 133 regulates power, generates alarm signals through the speaker 137 embedded into the wireless ear plug 101, and accesses the memory 132, including storing and retrieving downloaded programmable alarm tones. The control circuitry 133 also generates "live" alarm signals that are received through the wireless interface 132 as alarm tones or messages. Finally, the clock 134 activates and times the user-settable alarm interval. In a further embodiment, a vibration circuit is incorporated to physically vibrate the wireless ear plug 1001 in response to an alarm signal, either in addition to or in lieu of the speaker 137. Other wireless ear plug circuitry and functionality are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A wireless ear plug system for providing a downloadable programmable personal alarm, comprising:
    an alarm circuit with a self-contained power source, comprising:
        a randomly accessible memory providing general purpose storage;
        a leadless interface to externally receive a user-settable time interval and a programmable alarm tone, which are both stored into the memory;

a clock circuit to activate and time the user-settable time interval;

a wireless interface to receive a radio frequency alarm signal through at least one of a IEEE 802.11 compliant protocol and a Bluetooth wireless communication protocol, wherein the radio frequency alarm signal comprises a programmable message that is stored into the memory;

an alarm circuit to retrieve from the memory and to generate the programmable alarm tone through an in-ear speaker, which is triggered by one of the clock circuit and the wireless interface respectively upon an expiry of the user-settable time interval and the receipt of the radio frequency alarm signal; and a message circuit to retrieve from the memory and to generate the programmable message through the in-ear speaker; and an ear plug shaped distally to house the in-ear speaker within an ear canal and shaped proximally to enclose the alarm circuit.

2. A wireless ear plug system according to claim 1, further comprising:

a radio frequency receiver to implement the wireless interface; and a radio frequency antenna electronically connected to the radio frequency receiver and structurally integral to the ear plug.

3. A wireless ear plug system according to claim 1, further comprising:

a vibration circuit to physically vibrate the ear plug, which is triggered by one of the clock circuit and the wireless interface respectively upon an expiry of the user-settable time interval and the receipt of the radio frequency alarm signal.

4. A wireless ear plug system according to claim 1, further comprising:

a base station comprising a leadless coupling configured to electronically connect to the leadless interface of the alarm circuit; and a programmer, comprising:
a set of stored downloadable programmable alarm tones;
a user interface operable to specify the user-settable time interval and to select one or more of the programmable alarm tones; and
an earplug interface to provide the user-settable time interval and the programmable alarm tone to the alarm circuit through the leadless coupling.

5. A wireless ear plug system according to claim 4, wherein the base station further comprises a charger, comprising at least one of:

an leadless wired charger, comprising:
a step-down converter to provide control over the power source of the alarm circuit; and
a voltage regulator to generate direct current applied to the power source through the step-down converter via the leadless coupling; and a leadless inductive charger, further comprising an inductive coupler to apply the power source through the step-down converter wirelessly via the leadless coupling.

6. A wireless ear plug system according to claim 4, further comprising:

a manual trigger operable to trigger the radio frequency alarm signal.

7. A wireless ear plug system according to claim 4, wherein the base station comprises:

a base wireless interface to transmit the radio frequency alarm signal;

a radio frequency transmitter to implement the base wireless interface; and a radio frequency antenna electronically connected to the radio frequency transmitter.

8. A wireless ear plug system according to claim 7, further comprising:

an external wired connector connected to the base wireless interface, wherein the base wireless interface transmits the radio frequency alarm signal in response to an alarm signal received via the external wired connector.

9. A wireless ear plug system according to claim 1, wherein the at least one programmable alarm tone comprises at least one of a conventional buzzer, bell, voice, music, and electronically-reproducible sound.

10. A wireless ear plug system according to claim 1, wherein the ear plug comprises at least one of a soft-coated ear piece shaped to fit into an ear canal and an ear piece shaped to fit conformably into a cavum conchae of an outer ear.

11. A method for constructing a wearable wireless ear plug for providing a downloadable programmable personal alarm, comprising:

integrating an alarm circuit with a self-contained power source by providing a randomly accessible memory providing general purpose storage, a leadless interface to externally receive a user-settable time interval and a programmable alarm tone, which are both stored into the memory, a clock circuit to activate and time the user-settable time interval, a wireless interface to receive a radio frequency alarm signal through at least one of a IEEE 802.11 compliant protocol and a Bluetooth communication protocol, wherein the radio frequency alarm signal comprises a programmable message that is stored into the memory, an alarm circuit to retrieve from the memory and to generate the programmable alarm tone through an in-ear speaker, which is triggered by one of the clock circuit and the wireless interface respectively upon an expiry of the user-settable time interval and the receipt of the alarm signal, and a message circuit to retrieve from the memory and to generate the programmable message through the in-ear speaker; and housing the alarm circuit in an ear plug shaped distally to house the in-ear speaker within an ear canal and shaped proximally to enclose the alarm circuit.

12. A method according to claim 11, further comprising:
implementing the wireless interface as a radio frequency receiver; and
electronically connecting a radio frequency antenna to the radio frequency receiver, wherein the radio frequency antenna is structurally integral to the ear plug.

13. A method according to claim 11, further comprising:
providing a vibration circuit to physically vibrate the ear plug, which is triggered by one of the clock circuit and the wireless interface respectively upon an expiry of the user-settable time interval and the receipt of the radio frequency alarm signal.

14. A method according to claim 11, further comprising:
providing a base station comprising a leadless coupling configured to electronically connect to the leadless interface of the alarm circuit; and
including a programmer in the base station, comprising:
storing a set of downloadable programmable alarm tones; and
providing a user interface operable to specify the user-settable time interval and to select one or more of the programmable alarm tones, and an earplug interface to provide the user-settable time interval and the programmable alarm tone to the alarm circuit through the leadless coupling.

15. A method according to claim 14, wherein the base station further comprises a charger, comprising at least one of:
providing an leadless wired charger, comprising a step-down converter to provide control over the power source of the alarm circuit, and a voltage regulator to generate direct current applied to the power source through the step-down converter via the leadless coupling; and
providing a leadless inductive charger, further comprising an inductive coupler to apply the power source through the step-down converter wirelessly via the leadless coupling.

16. A method according to claim 14, further comprising:
incorporating a manual trigger into the base station operable to trigger the radio frequency alarm signal.

17. A method according to claim 14, further comprising:
providing a base wireless interface on the base station to transmit the radio frequency alarm signal, comprising a radio frequency transmitter to implement the base wireless interface, and a radio frequency antenna electronically connected to the radio frequency transmitter.

18. A method according to claim 17, further comprising:
connecting an external wired connector to the base wireless interface, wherein the base wireless interface transmits the radio frequency alarm signal in response to an alarm signal received via the external wired connector.

19. A method according to claim 11, wherein the at least one programmable alarm tone comprises at least one of a conventional buzzer, bell, voice, music, and electronically-reproducible sound.

20. A method according to claim 11, wherein the ear plug comprises at least one of a soft-coated ear piece shaped to fit into an ear canal and an ear piece shaped to fit conformably into a cavum conchae of an outer ear.

21. A wearable wireless ear plug system, comprising:
a wireless ear plug shaped distally to house an in-ear speaker within an ear canal and shaped proximally to enclose an alarm circuit, wherein the alarm circuit comprises a self-contained power source and further comprises:
a randomly accessible memory providing general purpose storage;
a leadless interface to externally receive a user-settable time interval and a programmable alarm tone, which are both stored into the memory;
a clock circuit to activate and time the user-settable time interval;
a wireless interface to receive a radio frequency alarm signal comprising a programmable message that is stored into the memory;
an alarm circuit to retrieve from the memory and to generate the programmable alarm tone through an in-ear speaker, which is triggered by one of the clock circuit and the wireless interface respectively upon an expiry of the user-settable time interval and a receipt of an alarm signal; and
a message circuit to retrieve from the memory and to generate the programmable message through the in-ear speaker; and
a base station comprising a recess configured to conformably receive the wireless ear plug and further comprising a leadless coupling configured to electronically connect to the leadless interface of the alarm circuit, comprising:
a programmer, comprising:
a set of stored downloadable programmable alarm tones;
a user interface operable to specify the user-settable time interval and to select one or more of the programmable alarm tones; and
an earplug interface to provide the user-settable time interval and the programmable alarm tone to the alarm circuit through the leadless coupling when the ear plug is received in the recess of the base station.

\* \* \* \* \*